US008852114B2

(12) United States Patent
Buxi et al.

(10) Patent No.: US 8,852,114 B2
(45) Date of Patent: Oct. 7, 2014

(54) HEART PULSE RATE MONITOR

(75) Inventors: Dilpreet Singh Buxi, Eindhoven (NL); Julien Penders, Luik (BE)

(73) Assignee: Stichting IMEC Nederland, Eindhoven (NL)

(*) Notice: Subject to any disclaimer, the term of this patent is extended or adjusted under 35 U.S.C. 154(b) by 696 days.

(21) Appl. No.: 12/974,865

(22) Filed: Dec. 21, 2010

(65) Prior Publication Data
US 2011/0152701 A1 Jun. 23, 2011

Related U.S. Application Data

(60) Provisional application No. 61/288,872, filed on Dec. 22, 2009.

(51) Int. Cl.
*A61B 5/02* (2006.01)
*A61B 5/024* (2006.01)

(52) U.S. Cl.
CPC .......... *A61B 5/02438* (2013.01); *A61B 5/02444* (2013.01)
USPC ....................................................... 600/500

(58) Field of Classification Search
USPC ................... 600/481, 485, 500–504
See application file for complete search history.

(56) References Cited

U.S. PATENT DOCUMENTS

| | | | |
|---|---|---|---|
| 4,409,983 A | 10/1983 | Albert | |
| 5,807,267 A * | 9/1998 | Bryars et al. | 600/500 |
| 6,099,478 A * | 8/2000 | Aoshima et al. | 600/500 |
| 6,491,647 B1 | 12/2002 | Bridger et al. | |
| 6,984,207 B1 * | 1/2006 | Sullivan et al. | 600/301 |
| 7,423,526 B2 * | 9/2008 | Despotis | 340/539.12 |
| 2004/0032957 A1 * | 2/2004 | Mansy et al. | 381/67 |

FOREIGN PATENT DOCUMENTS

FR 2700684 A1 7/1994

OTHER PUBLICATIONS

European Search Report, European Patent Application No. 10196384.1 dated Mar. 16, 2011.

* cited by examiner

*Primary Examiner* — Michael D'Angelo
(74) *Attorney, Agent, or Firm* — McDonnell Boehnen Hulbert & Berghoff LLP

(57) ABSTRACT

Disclosed herein are methods and devices for monitoring a heartbeat. In one embodiment, the device may comprise a sensor package mountable over a pulse location of a user. The sensor package may include a first sensor element configured to sense at least one signal at the pulse location and to provide a first output signal comprising a heart pulse signal and a first set of noise artifacts, a second sensor element configured to sense at least one signal at the pulse location and to provide a second output signal indicative of a second set of noise artifacts, and a mechanically isolating material located between the first sensor element and the second sensor element. The device may further comprise processing circuitry connected to the sensor package and configured to extract the heart pulse signal from the first output signal based on the first output signal and the second output signal.

23 Claims, 5 Drawing Sheets

HEART PULSE RATE MONITOR

CROSS-REFERENCE TO RELATED APPLICATIONS

This application claims priority of U.S. Provisional Application 61/288,872 filed Dec. 22, 2009, the contents of which are incorporated by reference herein in their entirety.

FIELD

The present disclosure relates to heart pulse monitors and is more particularly concerned with such monitors that can be worn at a convenient location by a user, for example, at the wrist.

BACKGROUND

Measuring the heart pulse rate (heartbeat) of a user is a topic of significant importance in personal health care, sports, stress monitoring, and other applications. If a heart pulse rate or heartbeat sensor can be packaged into a device, for example, a wristwatch, the sensor can be worn in a convenient position for the user. Such a device can be worn for activities ranging from intensive sports to sleeping.

Heart pulse rates provide information about the general health status of an individual and can indicate his or her general fitness, mental state, and/or level of physical activity. In addition, heart pulse rates can be used to detect cardiac arrhythmia, such as bradychardia and tachycardia for instance. Heart pulse rates also provide information about other specific medical conditions, such as the onset of an epileptic seizure, for instance.

Besides heart pulse and heart pulse rate monitoring, the heart rate variability (HRV) is also of significant interest. It is often claimed that the HRV carries information about autonomic regulation of cardiac activity. It is believed that, as a result of an arousing event, the heart rate will increase, in order to prepare the body for physical activity. In addition, it has been shown that the HRV has the potential to indicate the quality of a person's sleep. Other investigations highlight the importance of using the HRV as a parameter in calculating stress in drivers or military personnel. HRV also has been known to be affected by smoking, alcohol and caffeine consumption, as well as age and gender. In diseases, HRV is known to be affected by myocardial infarction, ventricular arrhythmias, hypertension, diabetes mellitus, and heart failure. Typically, analysis of the HRV is done using what is called a "footprint," which is a recording of the heart rate (HR) and HRV over a period of 24 hours.

However, obtaining an accurate measurement of an active person's pulse rate at the wrist is a complex process. This is because of the presence of artefacts produced by body motion. These artefacts are detected by the heart pulse sensor as noise. In many cases, this noise can produce signals of sufficient amplitude to completely mask the heart pulse signal which is to be measured.

U.S. Pat. No. 5,807,267 (Bryars et al.) discloses a heart rate monitor that is included in a wrist band. The heart rate monitor comprises two piezoelectric sensors arranged in a side-by-side configuration and is placed so that the sensors detect a pulse in an artery over which the sensors are placed. One of the sensors is used as a primary sensor and the other as a reference or background sensor. Signals generated by the reference or background sensor are digitally subtracted from signals generated by the primary sensor. The subtraction of the two signals reduces the effects due to motion of the user whilst using the heart rate monitor.

SUMMARY

In one embodiment, the device may comprise at least one sensor package mountable over a pulse location of a user. The sensor package may include a first sensor element configured to sense at least one signal at the pulse location and to provide a first output signal comprising a heart pulse signal and a first set of noise artefacts, a second sensor element configured to sense at least one signal at the pulse location and to provide a second output signal indicative of a second set of noise artefacts, and a mechanically isolating material located between the first sensor element and the second sensor element. The device may additionally comprise processing circuitry connected to each of the at least one sensor packages, the processing circuitry being configured to extract the heart pulse signal from the first output signal based on at least the first output signal and the second output signal.

In one embodiment, at least one of the first sensor element and the second sensor element may comprise a piezoelectric sensor element. In one embodiment, each piezoelectric sensor element may comprise a polyvinylidene fluoride (PVDF) film sensor element.

In one embodiment, the first sensor comprises a first material and the second sensor comprises a second material. The first material and the second material may each have an acoustic impedance that is matched to an acoustic impedance of the user's tissue. Alternately, the first material may be different from the second material and one of the first material and the second material may have an acoustic impedance that is matched to an acoustic impedance of the user's tissue while the other of the first material and the second material may have an acoustic impedance that is mismatched to the acoustic impedance of the user's tissue.

In one embodiment, the processing circuitry may comprise a microprocessor in which at least one of the first output signal, the second output signal, and the extracted heart pulse signal may be stored. Alternately or additionally, the processing circuitry may comprise filtering circuitry configured to filter at least one of the first output signal and the second output signal. Alternately or additionally, the processing circuitry may comprise analogue-to-digital circuitry for converting the extracted heart pulse signal into a digital signal. Alternately or additionally, the processing circuitry may comprise wireless transmission equipment for transmitting at least the extracted heartbeat signal to an external device.

In one embodiment, the device may further comprise a strap for attaching the device to the user. Alternately or additionally, the device may comprise an oximeter configured to determine a level of oxygen in blood of the user and to provide the level of oxygen to the processing circuitry.

In one embodiment, the at least one sensor package may comprise a plurality of sensor packages, the plurality of sensor packages being arranged in an array.

In another embodiment, the device may comprise a first packaging layer adjacent to skin of a user, a first sensor adjacent to the first packaging layer, the first sensor being configured to sense a primary set of signals comprising at least a heartbeat signal and a first set of noise artefacts, a second packaging layer adjacent to at least one of the first packaging layer and the primary sensor, a second sensor adjacent to the second packaging layer, the second sensor being configured to sense a reference set of signals comprising at least a second set of noise artefacts, a third packaging layer adjacent to at least one of the second packaging layer and the second sensor, and a strap for attaching the device to the user, the strap being adjacent to the third packaging layer.

In one embodiment, the first packaging layer may serve to electrically isolate the skin from the first sensor. Alternately or additionally, the second packaging layer may serve to mechanically decouple the first sensor and the second sensor. Alternately or additionally, the third packaging layer may serve to allow at least one of the first sensor and the second sensor to deform in response to the heartbeat signal.

In one embodiment, at least one of the first sensor and the second sensor may comprise a piezoelectric sensor.

In an embodiment of the method, the method may comprise using a primary sensor element to sense a first set of signals comprising at least a heart pulse signal and a first set of noise artefacts. The method may additionally comprise using a reference sensor element to sense a second set of signals comprising at least a second set of noise artefacts. Further, the method may comprise, based on the second set of noise artefacts, removing the first set of noise artefacts from the first set of signals so as to isolate the heart pulse signal. The method may further comprise transmitting the heart pulse signal to an external device.

BRIEF DESCRIPTION OF THE DRAWINGS

For a better understanding of the present disclosure, reference will now be made, by way of example only, to the accompanying drawings.

DETAILED DESCRIPTION

Figure 1:
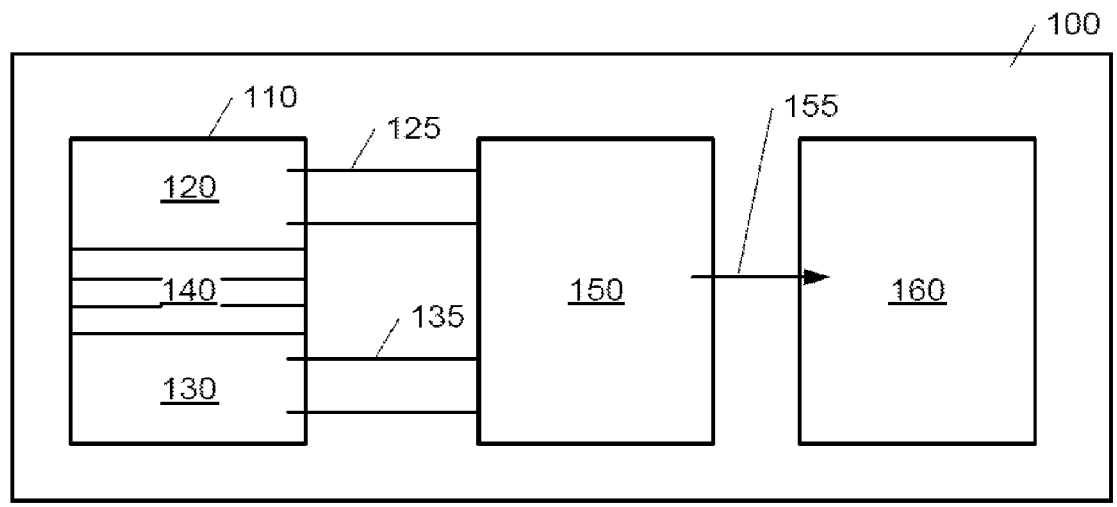
FIG. 1 illustrates a block diagram of a sensor arrangement in accordance with an embodiment of the present disclosure.

The present disclosure will be described with respect to particular embodiments and with reference to certain drawings but the disclosure is not limited thereto. The drawings described are only schematic and are non-limiting. In the drawings, the size of some of the elements may be exaggerated and not drawn on scale for illustrative purposes.

The heart pulse monitor device disclosed herein may readily be worn by a user and may allow for reliable extraction of relevant medical data.

Referring initially to FIG. 1, a heartbeat monitoring device 100 in accordance with an embodiment of the present disclosure is shown. As shown, the device 100 comprises a sensor package 110 that can be arranged adjacent to a pulse location of the user. One example of a pulse location is a wrist of the user. Other pulse locations are possible as well.

The sensor package 110 is shown comprising a first sensor 120 and a second sensor 130. Each of the first sensor 120 and the second sensor 130 may be configured to detect a heartbeat and/or one or more noise artefacts at the pulse location. To this end, one or both of the first sensor 120 and the second sensor 130 may be a piezoelectric sensor. Other sensors are possible as well. Each of the first sensor 120 and the second sensor 130 may be configured to provide one or more output signals to processing circuitry 150.

As shown, the first sensor 120 and the second sensor 130 may be separated by a layer 140 of mechanically isolating material positioned between the first sensor 120 and the second sensor 130. The layer 140 of mechanically isolating material may be made of, for example, silicone or another suitable compliant polymer foam or gel. Other materials are possible as well.

The first sensor 120 may comprise a first mechanical sensor and may be configured to sense one or more signals at the pulse location and to provide a first output signal 125 to processing circuitry 150 for processing. The first output signal 125 may include one or more heartbeat signals and/or one or more sets of noise artefacts at the pulse location. The one or more heartbeat signals and/or one or more sets of noise artefacts may be mixed together in the first output signal 125, such that the one or more heartbeat signals cannot be determined by simply viewing the first output signal 125. The one or more sets of noise artefacts included in the first output signal 125 may be independent of the one or more heart beat signals.

Similarly, the second sensor 130 may comprise a second mechanical sensor and may be configured to sense one or more signals at the pulse location and to provide a second output signal 135 to the processing circuitry 150 for processing. The second output signal 135 may include to one or more artefact signals at the pulse location. The one or more sets of noise artefacts included in the second output signal 135 may be independent of the one or more heart beat signals included in the first output signal 125. Additionally, the one or more sets of noise artefacts included in the second output signal 135 may be correlated with the one or more sets of noise artefacts included in the first output signal 125.

As shown, the sensor package 110 is connected to processing circuitry 150. The processing circuitry 150 may be configured to produce an output signal 155 based at least in part on the first and second output signals 125, 135. The output signal 155 may be indicative of the heartbeat of the user of the device 100. As an example, the output signal 155 may be the extracted heartbeat signal. As another example, the output signal 155 may be a function of the heartbeat rate at which the first output signal 125 is received. Note that the heartbeat may also be used, for example, to measure the intensity or the presence of a pulse.

The processing circuitry 150 may be configured to extract the heartbeat signal from the first output signal 125 based on the first output signal 125 and the second output signal 135. To this end, the processing circuitry 150 may comprise at least one microprocessor that operates for both processing the first and second signals 125, 135 and storing one or more of the first and second output signals 125, 135 and the processed output signal 155.

In some embodiments, the processing circuitry 150 may further comprise filtering circuitry for filtering the first and output second signals using, for example, Butterworth or Chebychev filters or any other suitable filtering technique. In some embodiments, the processing circuitry 150 may include adaptive filtering circuitry to allow adaptive filtering of the first and second output signals 125, 135, as described below.

Additional filtering circuitry may also be included to improve the effectiveness of the adaptive filtering algorithm.

In some embodiments, the processing circuitry 150 may further include one or both of a non-inverting amplifier and an analog-to-digital converter (ADC). In these embodiments, the output signal 155 may be a digital output signal. It will be understood that the amplifier may be used alone or in combination with the ADC. Similarly, the ADC may be used alone or in combination with the amplifier.

In some embodiments, the processing circuitry 150 may further comprise an integrated radio and antenna or other equipment for wirelessly transmitting data to an external device. In some embodiments, the data may be data related to one or more of the first output signal 125, the second output signal 135, and the output signal 155, and the external device may be a display device or a base station of a body area network. Other examples are possible as well. In some embodiments, the data may be transmitted to a central point for review and interpretation.

The heartbeat monitoring device 100 may also include a display 160 that displays the output signal 155 in a form that can readily be understood by the user. As an example, the output signal 155 may be the extracted heartbeat signal, and the display 160 may display the extracted heartbeat signal in the form of beats per minute. Other examples are possible as well.

Figure 2:
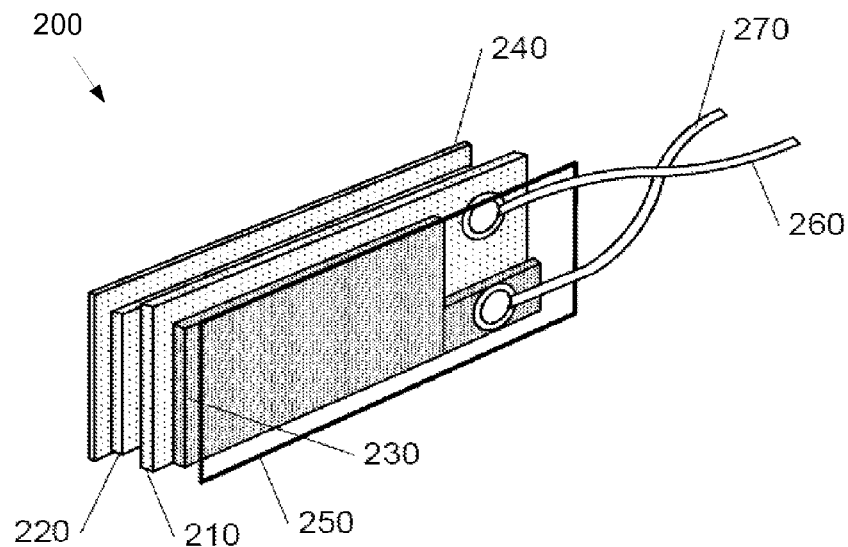
FIG. 2 illustrates a perspective view of a sensor arrangement in accordance with an embodiment of the present disclosure.

FIG. 2 illustrates a perspective view of a sensor arrangement in accordance with an embodiment of the present disclosure. In FIG. 2, a commercially available polyvinylidene fluoride (PVDF) sensor 200 is shown. The sensor 200 is an example sensor that may be integrated into the heartbeat monitoring device described above. The PVDF may be, for example, around 75 μm thick. The sensor 200 is shown comprising a PVDF film layer 210 that is located between two metallised coating layers 220, 230. Protective coating layers 240, 250 are located on the outside of the two metallised coating layers 220, 230. Leads 260, 270 provide connections to a sensor (not shown).

In some embodiments, the metallised coating layers 220, 230 may comprise silver or another conductive material that may act as an electrode for a lead, such as the lead 270, as shown. The lead 270 may serve to electrically connect the PVDF sensor to an analogue amplifier (located in, for example, the processing circuitry 150 of FIG. 1).

In some embodiments, the protective coating layers 240, 250 may serve to prevent mechanical damage to the metallised coating layers or another part of the PVDF sensor 200.

In some embodiments, the leads 260, 270 may allow the correlation of noise and prevent transfer of heartbeat signal energy to the reference sensor. To this end, it may be desirable to have high electrical conductivity between the PVDF sensor and the leads 260, 270 themselves so as to increase an SNR of the output traces. Additionally, it may be desirable for the leads 260, 270 to have a small volume may be desired so that the attachment does not interfere with heartbeat acquisition. Flexibility, mechanical strength and long-term stability are other features that may be selected appropriately.

The leads 260, 270 may be attached to the sensor 200 using one or more known attachment techniques. Examples of attachment techniques include penetrative and non-penetrative attachment. Penetrative techniques typically involve using rivets, screws or crimp connectors that pierce through the film. Sometimes, an additional reinforcing laminate material is placed to increase contact strength. The metallisation on the film could be patterned or displaced such that the electrodes on both sides of the film do not effectively form a short circuit. Crimp connectors are known for their flexibility.

Non-penetrative methods involve using low-melting point alloys such as tin, bismuth and indium to adhere the leads to the sensor 200 or placing conductive rubber on either side of the film.

Figure 7:
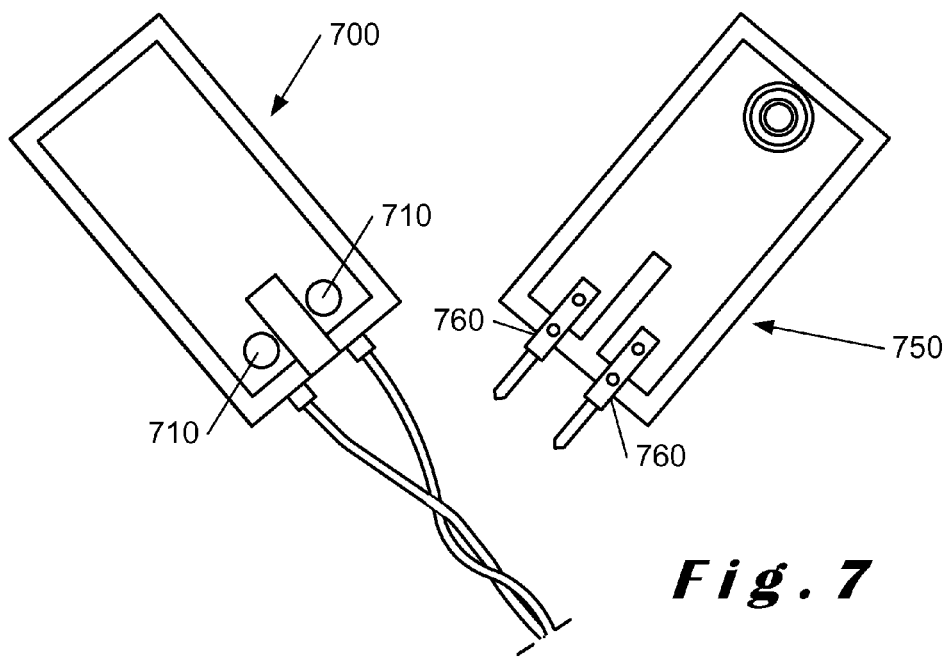
FIG. 7 illustrates possible lead attachments for the sensor package of FIG. 5.

FIG. 7 shows examples of two kinds of lead attachments. The sensor 700 on the left is shown with rivets 710. The sensor 750 on the right is shown with crimp connectors 760. Other types of lead attachments are possible as well.

Figure 3:
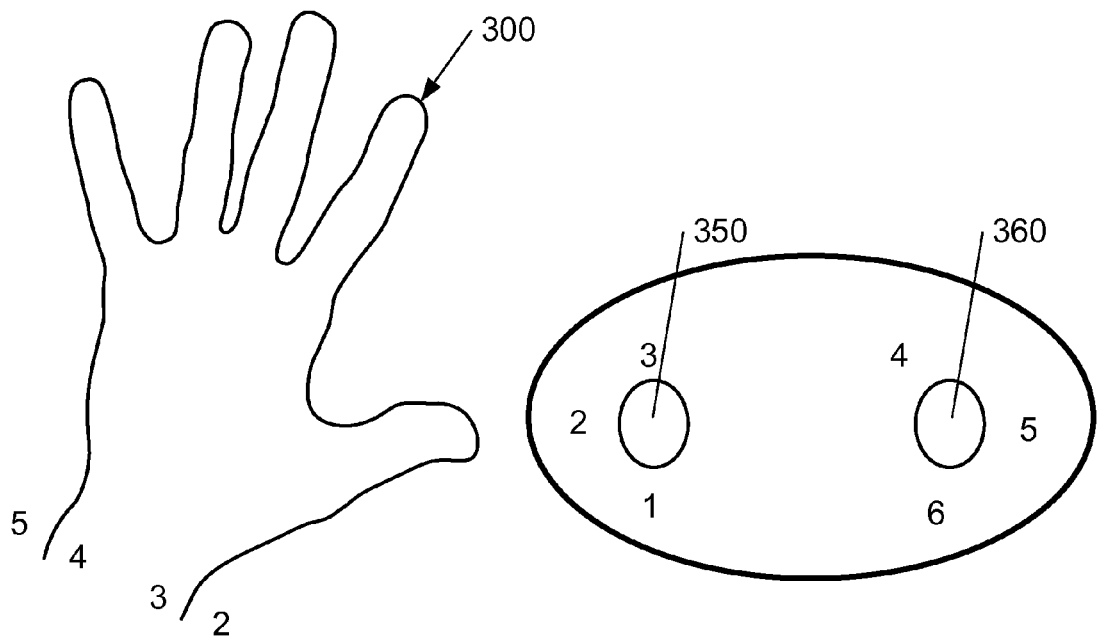
FIG. 3 illustrates possible locations of sensor elements in relation to a user's wrist.

FIG. 3 illustrates possible locations of sensor elements in relation to a user's wrist. It will be appreciated that the heart pulse rate or heartbeat of a user must be detected at a suitable location for the sensor in accordance with the present disclosure to be able to detect and provide the desired signal output. A hand 300 of a user is shown with locations '2', '3', '4', '5' labeled at the wrist. FIG. 3 also shows a cross-section of the wrist of hand 300. Locations '2', '3', '4', '5' are shown on the cross-section, as well as additional locations '1' and '6'. Further, two pulse positions 350 and 360 are shown.

The optimal placement of a sensor may depend on the position of the hand 300. For example, if the hand 300 is positioned on a table (not shown) with the palm facing downwards towards the surface of the table, it may be desirable to use locations '3' and '4' to detect heart pulse rate or heartbeat. As another example, if the hand 300 clenched in a fist with the palm facing upwards away from the surface of the table (not shown), location '2' may be more suitable for the detection of heart pulse rate or heartbeat. Other possible locations, such as, '1', '5' and '6' may also be used.

Figure 4:
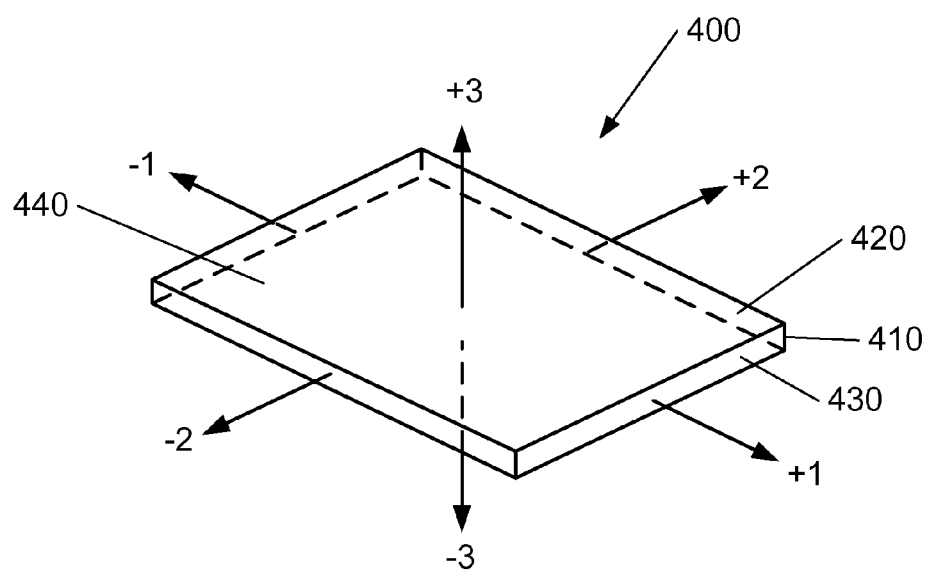
FIG. 4 shows a sensor element illustrating possible directions of force and electric voltage generation within a sensor element.

FIG. 4 shows a sensor element illustrating possible directions of force and electric voltage generation within a sensor element. As shown, the sensor element 400 comprises a PVDF film 410 located between metallised coating layers 420, 430. The charge, $Q_3$, accumulated between the metallised coating layers 420, 430 is proportional to the surface area of the metallised coating layers (indicated as 440), the piezoelectric constant, $g_{33}$, and the average strain, $S_{average}$, in the thickness direction. The thickness direction is indicated by +3 to −3.

This relation may be expressed analytically by the following equation:

$$Q_3 = AS_{average} g_{33} \Delta$$

where $\Delta$ is the thickness of the PVDF film.

The voltage, V, between the metallised coating layers 420, 430, which forms the output signal of the sensor, is proportional to the charge, $Q_3$, and the capacitance, C, of the piezoelectric film. This relation may expressed analytically by the following equation:

$$V = \frac{Q_3}{C}$$

It may be understood that a smaller sensor area typically corresponds to a smaller area over which the strain is integrated, resulting in a more local strain captured by the sensor. For this reason, it may be desirable to use a smaller sensor area to the extent possible.

It may be further understood that, while it is desirable to correlate motion signals from the primary sensor and a reference signal as much as possible, it is also be necessary to prevent the heart pulse rate or heartbeat signal energy from reaching the reference sensor. This is because it is possible that adaptive filtering, if used, will remove both motion and heartbeat information during filtering.

Figure 5:
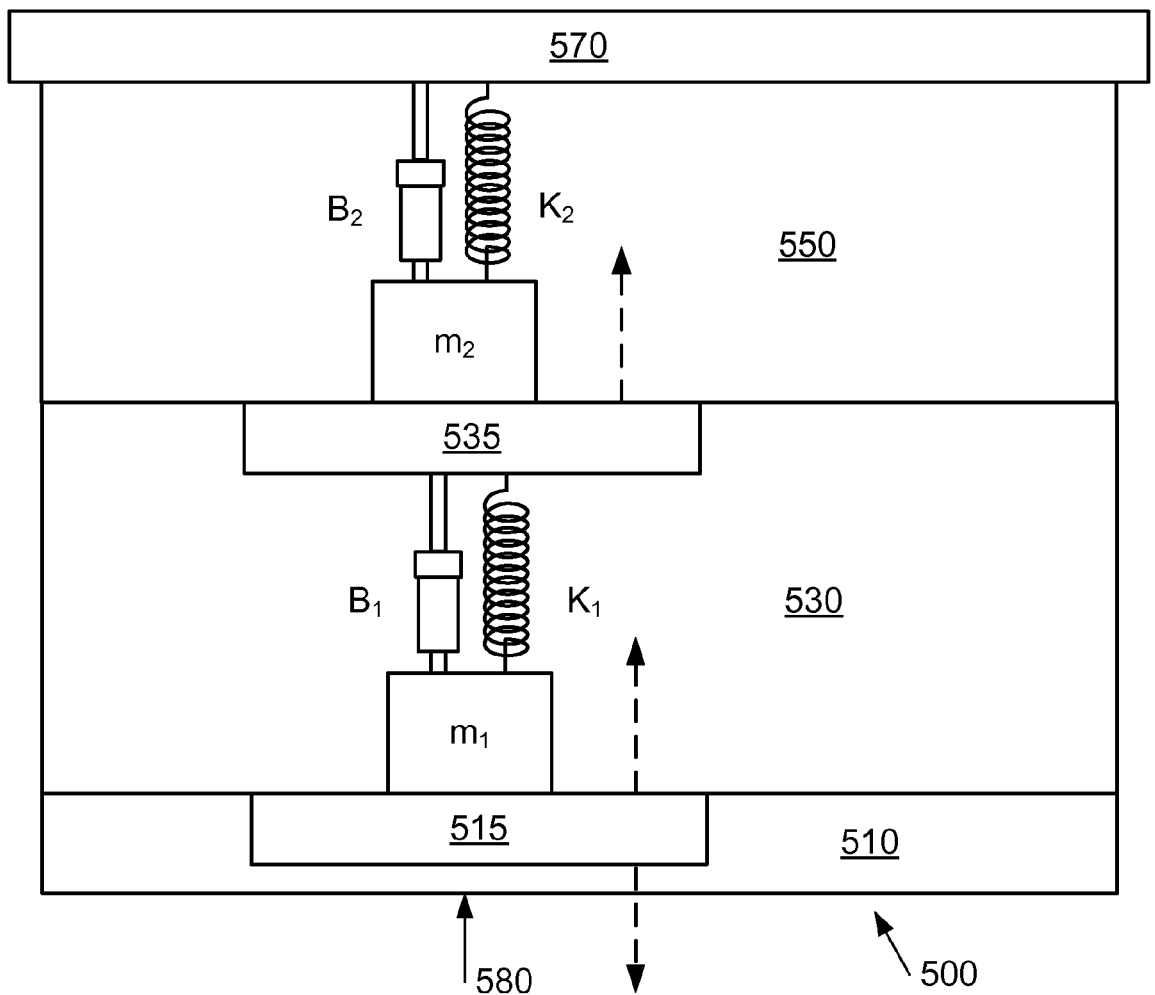
FIG. 5 illustrates a schematic diagram of a sensor package in accordance with an embodiment of the present disclosure.

FIG. 5 illustrates a schematic representation of a sensor package 500 in accordance with an embodiment of the present disclosure. The sensor package 500 comprises three packaging layers: a first packaging layer 510, a second packaging layer 530, and a third packaging layer 550, each of which serves a different purpose in the sensor package 500.

The first packaging layer 510 is shown comprising a first sensor 515, the primary sensor, and is configured to be located next to the skin of a user (not shown). The second packaging layer 530 is shown comprising a second sensor 535, the reference (background) sensor, and is configured to be located between the first packaging layer 510 and the third packaging layer 550. The third packaging layer 550 is arranged to be adjacent to a strap 570 or other mechanism for holding the sensor package 500 against the wrist (or other pulse location) of the user. One or both of the first sensor 515 and the second sensor 535 may be piezoelectric sensors or transducers.

The material of the second and third packaging layers 530, 550 can be represented, from the mechanical point of view, as respective mass-spring-damper arrangements, as shown. However, the second packaging layer 530 has a different purpose than the third packaging layer 550, as noted above.

As shown in FIG. 5, the material from which the second packaging layer 530 is made can be defined by constants $m_1$, $B_1$, and $k_1$, where $m_1$ is the mass, $k_1$ is the spring constant, and $B_1$ is the damping constant of the material of the second packaging layer 530.

Similarly, the material from which the third packaging layer 550 is made can be defined by constants $m_2$, $B_2$, and $k_2$, where $m_2$ is the mass, $k_2$ is the spring constant, and $B_2$ is the damping constant of that particular material. These constants $m_1$, $m_2$, $k_1$, $k_2$, $B_1$ and $B_2$ are determined by the type of material and its specific dimensions within the sensor package 500. The sensor 535 is assumed to have negligible mass due to its small thickness, for example, 40 μm.

While not shown, the strap 570 may also be represented by a mass-spring-damper arrangement with a mass $m_3$, a spring constant $k_3$, and a damping constant $B_3$. Here, these constants are determined by the material from which the strap 570 is made, the dimensions of the strap, and its tightness against the wrist of the user.

The material of the first packaging layer 510 may act as an insulation layer between the skin of the user's wrist and the first sensor 515, electrically isolating the skin from the first sensor 515. In this manner, the first packaging layer 510 may prevent signal distortion due to electrostatic coupling between the skin and the first sensor 515.

The material of the second packaging layer 530 may serve to prevent the second sensor 535 from being deformed due to heart pulse rate or heartbeat related vibrations. It effectively decouples the first sensor 515 from the second sensor 535. For this purpose, the material for packaging layer 530 may comprise a material having a spring constant $k_1$ that is relatively small in order to decouple mechanically the heart rate pulse or heartbeat vibration from the sensor 535. It will be appreciated that any material can be used that provides the desired spring constant.

The material of the third packaging layer 550 may serve to provide a reaction force for the first sensor 515 and the second sensor 535 and may allow each of the sensors 515, 535 to deform in accordance with a detected heart pulse rate or heartbeat of the user, whilst isolating both of the sensors 515, 535 from motion forces due to the strap 570.

In some embodiments, the sensor package 500 may additionally include one or more leads, such as the leads described above in connection with FIG. 2. The leads may have a low mass to avoid corruption of the signals due to mechanical vibration of the masses.

It is to be understood that, depending on the material constants, the sensors 515, 535 may be interchanged. That is, either the first sensor 515 or the second sensor 535 may serve as a primary sensor, and the other of the first sensor 515 and the second sensor 535 may serve as a reference sensor.

In either case, the primary sensor may be configured to detect one or more heart pulse rate or heartbeat signals of the user as well as one or more artefact signals. The signals detected by the primary sensor may be output by the primary sensor as a first output trace. The reference sensor may be configured to detect one or more artefact signals. The signals detected by the reference sensor may be output by the reference sensor as a second output trace.

In cases where there is motion and the primary and reference sensors detect artefact signals that correlate with one another, the artefact signals may be removed from the first output trace, and a heartbeat signal may be detected. This process is illustrated in FIG. 6.

Figure 6:
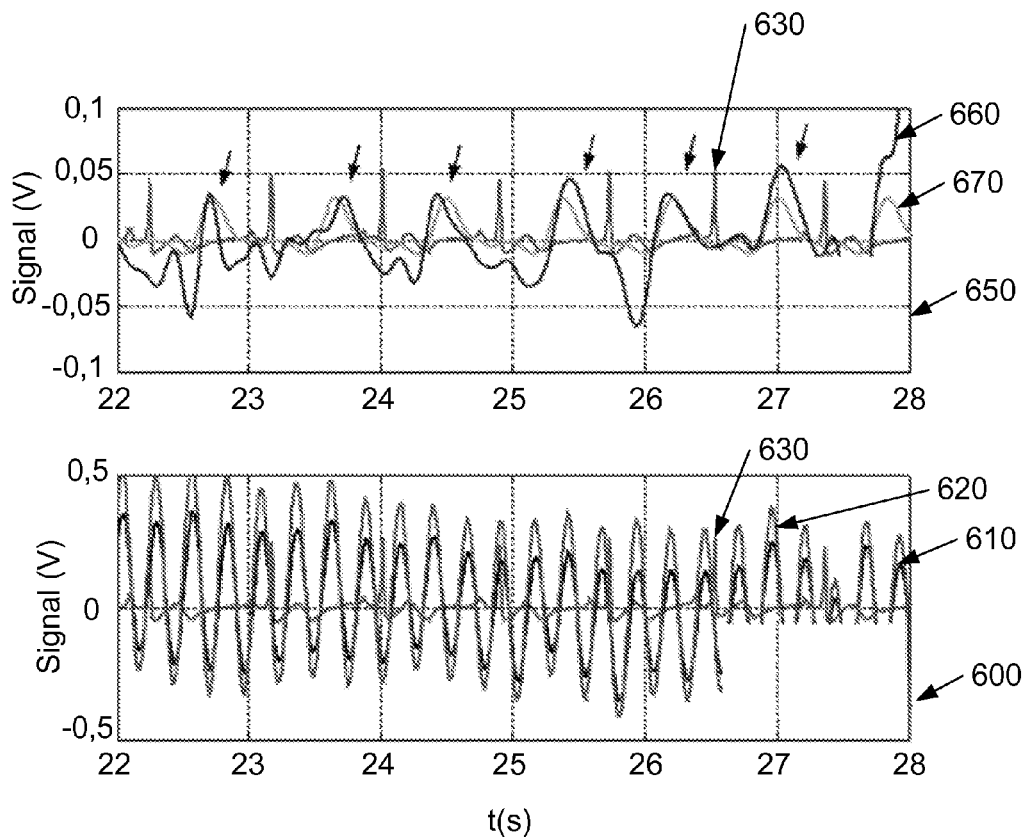
FIG. 6 illustrates output traces from the sensor of FIG. 5.

FIG. 6 illustrates output traces from the sensor of FIG. 5. In FIG. 6, two plots 600, 650 are shown.

In plot 600, signals obtained with the sensor package located at position '1' are shown for a specified period of time. Trace 610 corresponds to the first output signal from the primary sensor, trace 620 corresponds to the second output signal from the reference sensor, and trace 630 corresponds to an electrocardiogram (ECG) signal. All traces are indicated as voltage signals during that specified period of time.

In plot 650, for the same specified period, trace 660 corresponds to an adaptive filter output signal and trace 670 corresponds to a template signal. Traces 660 and 670 are shown together with the ECG signal 630 from plot 600.

Motion artefacts are a problem in wrist-based heart rate measurement. A differential measurement with appropriate sensor packaging may eliminate motion artefact. In accordance with the present disclosure, the measurement system is effectively divided into four parts, namely, the sensor packaging, the lead attachments, the readout circuitry and the signal processing.

Signal processing is discussed first, as the requirements for the input signals place requirements on the rest of the system. Several signal processing algorithms may be used but each one needs to be compared for its ability to reduce motion artefact in a non-stationary environment. These signal processing algorithms may include one or more of independent and principal component analyses, spatial averaging, and adaptive filtering. It will be appreciated that each of these signal processing algorithms may be implemented separately or may be implemented as a combination in accordance with a particular application. Each of these signal processing algorithms are discussed below.

Independent and principle component analyses are examples of algorithms that take multiple output traces from several sensors as an input and may separate the signals components of the multiple output traces to produce one or more outputs. As an example, the output traces from the sensors may include both motion artefact and heartbeat signal components mixed in unknown quantities. The algorithms may take the output traces as an input and may separate the motion artefact and heartbeat signals to produce an output of at least a heartbeat signal.

Spatial averaging involves summing and dividing two or more output traces in order to obtain two or more averaged signals. This averaging process may be weighted or non-weighted.

Adaptive filtering involves two output traces, with one acting as a primary and the other as a reference. The primary output trace may include a signal plus noise ($s+n_o$), whereas the reference output trace may contain only noise ($n_f$, uncorrelated with s but correlated in some unknown way with the noise, $n_o$). Each of $s+n_o$ and $n_f$ may be provided to a canceller. The noise $n_f$ may then be filtered to produce an output, y, that is as close a replica as possible of the noise, $n_o$. This output, y, may then be subtracted from the primary input, $s+n_o$, to produce the system output or adaptive filtered signal, $e=s+n_o-y$, which should ideally only contain the signal s. It can be seen that if the primary output trace comprises both a heartbeat signal (s) and motion artefacts ($n_o$) and the reference output trace comprises motion artefacts ($n_f$) correlated in some way with the motion artefacts of the primary output trace ($n_o$), adaptive filtering may be used to extract the heartbeat signal, s. It is assumed that the signal (s) and the noise ($n_o$) are statistically independent of each other and the noise in the reference input ($n_f$) correlates strongly with the noise ($n_o$) in the primary input. Other than this, no other knowledge is required about any of the input signals.

The adaptive filter assumes statistical independence between the signal and noise sources and a strong correlation between the noise signals in the reference and primary inputs respectively. The reference input should therefore acquire only the motion signal and not the heartbeat signal. Otherwise, a portion of the signal energy representing the heartbeat will also be removed by the adaptive filter, decreasing a signal-to-noise ratio (SNR) or other quality metric of the output heartbeat signal. The preferred approach to fulfil these requirements on the input signals is to decrease the sensor size, while packaging the primary and reference sensors appropriately. Note that the smaller sensor area allows both sensors to be placed closer to each other, ensuring better correlation of motion measured in both sensors, thereby better fulfilling the assumption of the adaptive filtering algorithm.

While different embodiments may make use of each of the above-described algorithms separately, a combination of the above-described algorithms may also be carried out, for example, spatial averaging followed by adaptive filtering or independent component analysis on the spatially averaged signals to reduce the amount of data during processing. Other algorithms may be used as well, alone or in combination with the above-described algorithms.

A pair of mechanical sensors with a layer of mechanically isolating material located between the first and second sensors, as described above, may allow the reference and primary sensors to stay in close proximity to each other while ensuring that the reference sensor captures signals that only relate to movement. As described above, PVDF film sensors with metal and polymer layers as packaging between the first and second sensors may be used. Several positions on the radial (thumb) side of the arm have been identified as possible locations to accommodate for the orientation of the arm in space. The packaging allows one sensor to act as a primary sensor by detecting both heart pulse or heartbeat related vibrations and motion artefacts, and allows the second sensor to act as a reference sensor by only detecting motion of the user. The signals from these sensors may be used in active noise cancellation involving an adaptive filter, as described above.

A wide variety of mechanical sensors exist. Piezoelectric sensors comprising PVDF, as described above, are one type of such a mechanical sensor. PVDF is biocompatible, can conform to the contours of the body, and possesses a high elastic compliance since it is a polymer. Its compliance and acoustic impedance matches that of human tissue, allowing heartbeat-related vibrations to be transferred effectively from the body of a user to the sensor. However, other materials, like nylon and polyvinyl chloride (PVC) also exhibit a similar mechanical effect and may be used in the sensors described above.

In some embodiments, the material of the sensors may be different. The acoustic impedances of one material may match the acoustic impedance of human tissue while the other may not. Lead zirconate titanate (PZT) is an example of a piezoelectric material whose acoustic impedance does not much the acoustic impedance of human tissue. Other examples are possible as well. This approach may be considered for body vibrations of significantly higher frequencies in the range of a few 10 kilohertz.

Figure 8:
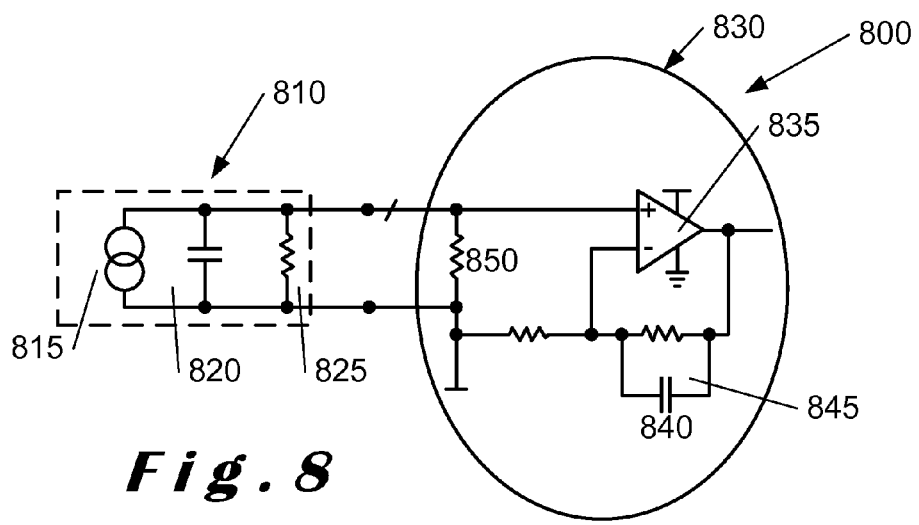
FIG. 8 illustrates a schematic diagram of a piezoelectric sensor and a signal conditioning circuit.

Piezoelectric sensors are self generating and do not require a current or voltage excitation. A piezoelectric sensor can, however, be modelled as a voltage or charge source, requiring respectively a voltage or a charge amplifier. FIG. 8 illustrates a piezoelectric sensor arrangement 800 that is modelled as a charge source.

In FIG. 8, the piezoelectric sensor arrangement 800 is shown comprising a piezoelectric sensor 810 and a signal conditioning circuit 830. The sensor 810 can be represented as a charge source 815 coupled in parallel to a shunt capacitor 820 and a resistor 825. Alternatively, not shown, the sensor 810 can be represented as a voltage source with a series capacitor and resistor.

The signal conditioning circuit 830 is shown comprising a non-inverting amplifier circuit 835 with a direct current (DC) biasing that may be used to amplify the sensor output signal. A capacitor 840, placed in parallel with one of the amplifying resistors 845, results in a first-order low pass filter which reduces electromagnetic interference. Resistor 850 provides a DC bias path for the single supply amplifier input stage 835 as shown.

Figure 9:
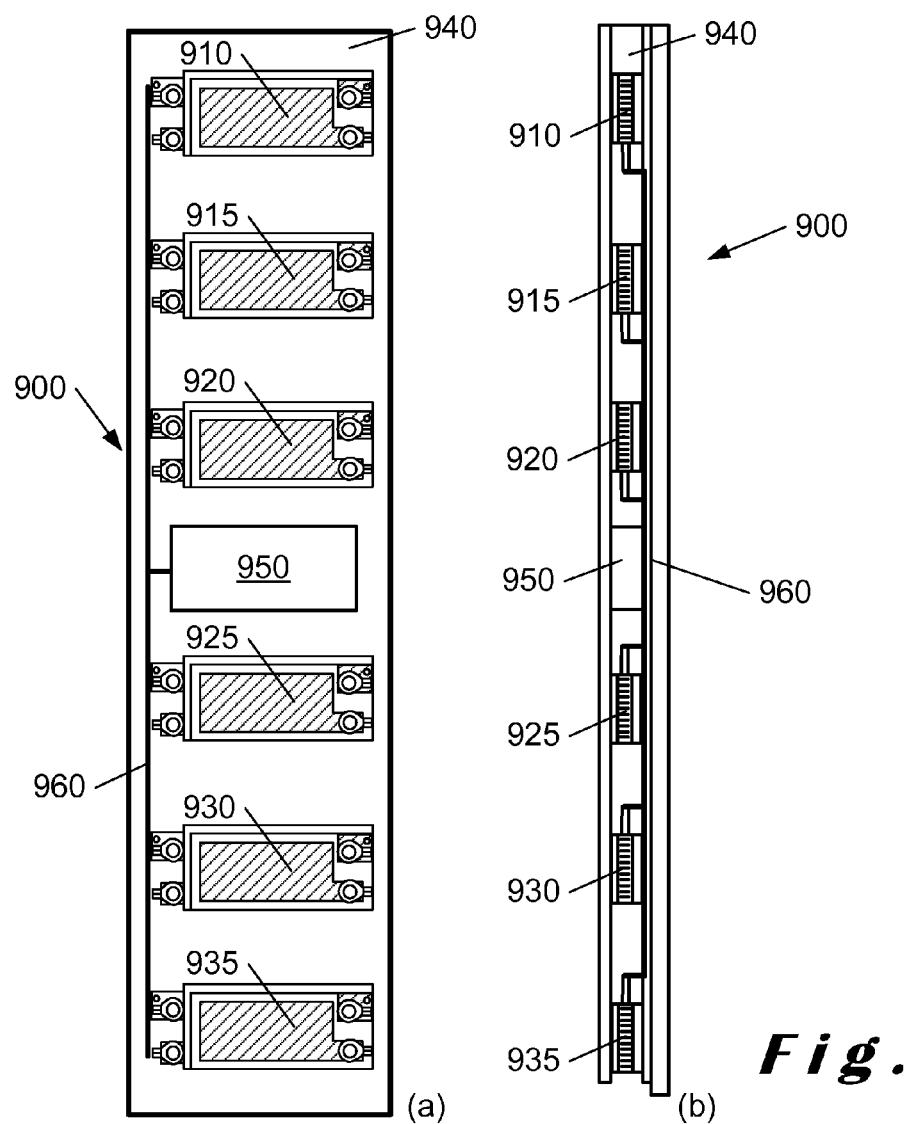
FIGS. 9(a) and 9(b) respectively illustrate a bottom view and a side view of an example of a heart rate monitor device comprising an array of sensor packages in accordance with an embodiment of the present disclosure.

In accordance with the present disclosure, the device may be packaged to be worn at the wrist. FIGS. 9(a) and 9(b) respectively illustrate a bottom view and a side view of an example of a heart rate monitor device comprising an array of sensor packages in accordance with an embodiment of the present disclosure.

In FIGS. 9(a) and 9(b), an array 900 of sensor packages 910, 915, 920, 925, 930, 935 as described above are shown attached to a wristlet 940. The wristlet 940 includes a housing 950 that contains a readout circuit (not shown) for both primary and reference sensors (also not shown) located in the sensor packages 910, 915, 920, 925, 930, 935.

It will readily be understood that the housing 950 also contains processing circuitry (not shown) for processing the signals provided by the primary and reference sensors in each of the sensor packages 910, 915, 920, 925, 930, 935. Connections between each sensor package 910, 915, 920, 925, 930, 935 and the housing 950 are shown by a communication bus 960 over which signals can be transmitted from each package 910, 915, 920, 925, 930, 935 to the housing 950.

In one embodiment, the housing 950 may additionally comprise data storage, such as optical or magnetic data storage, in which signals recorded by the primary and reference sensors may be stored. The data storage may be comprised by, for example, an element of the processing circuitry, such as a microprocessor. The signals stored in the data storage may subsequently be read out to an external device, such as a processing device, a display, or an intermediate device such as a base station. The signals may be read out to the external device via a wired or wireless link.

In one embodiment of the present disclosure, the signals output from the primary and reference sensors comprise analog signals. These analog signals may be converted into digital signals for transmission via a wired or wireless link to, for example, an external display or a base station.

In another embodiment, in order to have good contact between sensors and skin so that the quality of the signals is maintained during ambulatory monitoring as well as comfort of the wearer, a piece of foam is placed between the reference sensor and the wrist band if the reference sensor is the sensor nearest to the wrist band.

The invention claimed is:

1. A heartbeat monitoring device comprising:
    at least one sensor package mountable over a pulse location of a user, wherein each sensor package includes:
    a first sensor configured to sense at least one signal at the pulse location and to provide a first output signal comprising a heartbeat signal and a first set of noise artefacts;
    (ii) a layer of isolating material located above the first sensor; and
    (iii) a second sensor located above the first sensor and configured to sense at least one signal at the pulse location and to provide a second output signal comprising a second set of noise artefacts; and
    processing circuitry connected to each of the at least one sensor package, the processing circuitry being configured to extract the heartbeat signal from the first output signal based on at least the first output signal and the second output signal.

2. The heartbeat monitoring device of claim 1, wherein at least one of the first sensor and the second sensor comprises a piezoelectric sensor.

3. The heartbeat monitoring device of claim 2, wherein each piezoelectric sensor comprises a polyvinylidene fluoride film sensor.

4. The heartbeat monitoring device of claim 1, wherein the first sensor comprises a first material and the second sensor comprises a second material.

5. The heartbeat monitoring device of claim 4, wherein the first material and the second material each have an acoustic impedance that is matched to an acoustic impedance of the user's tissue.

6. The heartbeat monitoring device of claim 4, wherein the first material is different from the second material.

7. The heartbeat monitoring device of claim 6, wherein one of the first material or the second material has an acoustic impedance that is matched to an acoustic impedance of the user's tissue, and the other of the first material or the second material has an acoustic impedance that is mismatched to the acoustic impedance of the user's tissue.

8. The heartbeat monitoring device of claim 1, wherein the processing circuitry comprises a microprocessor in which at least one of the first output signal, the second output signal, or the extracted heartbeat signal is stored.

9. The heartbeat monitoring device of claim 1, wherein the processing circuitry comprises filtering circuitry configured to filter at least one of the first output signal or the second output signal.

10. The heartbeat monitoring device of claim 1, wherein the processing circuitry comprises analogue-to-digital circuitry for converting the extracted heartbeat signal into a digital signal.

11. The heartbeat monitoring device of claim 1, wherein the processing circuitry comprises wireless transmission equipment for transmitting at least the extracted heartbeat signal to an external device.

12. The heartbeat monitoring device of claim 1, further comprising a strap for attaching the device to the user.

13. The heartbeat monitoring device of claim 1, further comprising an oximeter configured to determine a level of oxygen in blood of the user and to provide the level of oxygen to the processing circuitry.

14. The heartbeat monitoring device of claim 1, wherein the at least one sensor package comprises a plurality of sensor packages, the plurality of sensor packages being arranged in an array.

15. The heartbeat monitoring device of claim 1, wherein the layer of isolating material comprises a mechanically isolating material configured to prevent the second sensor from being deformed due to heartbeat-related vibrations.

16. The heartbeat monitoring device of claim 15, wherein the layer of isolating material comprises the second sensor.

17. The heartbeat monitoring device of claim 1, further comprising a layer of material on top of the second sensor and configured to provide a reaction force for the first sensor and the second sensor, thereby allowing each of the first sensor and the second sensor to deform in accordance with a detected heart pulse rate of heartbeat of the user.

18. A heartbeat monitoring device, comprising:
    a first packaging layer adjacent to skin of a user;
    a first sensor above the first packaging layer, the first sensor being configured to sense a primary set of signals comprising at least a heartbeat signal and a first set of noise artefacts;
    a second sensor above the first sensor, the second sensor being configured to sense a reference set of signals comprising at least a second set of noise artefacts, wherein the first sensor and the second sensor are arranged in a vertical stack over a horizontal plane defined by the skin;
    a second packaging layer between first sensor and the second sensor;
    a third packaging layer above the second sensor; and
    a strap for attaching the device to the user, the strap being adjacent to the third packaging layer.

19. The heartbeat monitoring device of claim 18, wherein the first packaging layer serves to electrically isolate the skin from the first sensor.

20. The heartbeat monitoring device of claim 18, wherein the second packaging layer serves to mechanically decouple the first sensor and the second sensor.

21. The heartbeat monitoring device of claim 18, wherein the third packaging layer serves to allow at least one of the first sensor and the second sensor to deform in response to the heartbeat signal.

22. The heartbeat monitoring device of claim 18, wherein at least one of the first sensor or the second sensor comprises a piezoelectric sensor.

23. A method for detecting a heartbeat signal, comprising:
    using a primary sensor to sense a first set of signals comprising at least a heartbeat signal and a first set of noise artefacts, wherein the primary sensor is positioned over a pulse location;
    using a reference sensor to sense a second set of signals comprising at least a second set of noise artefacts, wherein the reference sensor is positioned substantially over the primary sensor;
    based on the second set of noise artefacts, removing the first set of noise artefacts from the first set of signals so as to isolate the heartbeat signal; and
    transmitting the heartbeat signal to a remote device.

* * * * *